United States Patent
Baril et al.

(10) Patent No.: US 11,116,488 B2
(45) Date of Patent: Sep. 14, 2021

(54) TISSUE GUARD FOR TISSUE REMOVAL AND OTHER SURGICAL PROCEDURES

(71) Applicant: Covidien LP, Mansfield, MA (US)

(72) Inventors: Jacob Baril, Norwalk, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 27 days.

(21) Appl. No.: 16/722,015

(22) Filed: Dec. 20, 2019

(65) Prior Publication Data

US 2021/0186476 A1 Jun. 24, 2021

(51) Int. Cl.
*A61B 1/32* (2006.01)
*A61B 17/02* (2006.01)
*A61B 90/00* (2016.01)

(52) U.S. Cl.
CPC .......... *A61B 17/0218* (2013.01); *A61B 90/04* (2016.02); *A61B 2090/0427* (2016.02); *A61B 2217/005* (2013.01)

(58) Field of Classification Search
USPC ........................................................ 600/205
See application file for complete search history.

(56) References Cited

U.S. PATENT DOCUMENTS

| | | |
|---|---|---|
| 5,578,000 A | 11/1996 | Greff et al. |
| 5,941,873 A | 8/1999 | Korenfeld |
| 6,033,362 A | 3/2000 | Cohn |
| 6,544,210 B1 | 4/2003 | Trudel et al. |
| 7,789,946 B2 | 9/2010 | Schultz et al. |
| 7,901,353 B2 * | 3/2011 | Vayser ............... G02B 23/2469 600/182 |
| 9,427,288 B1 | 8/2016 | Chenger et al. |
| 10,076,358 B2 | 9/2018 | Zergiebel et al. |
| 2005/0054993 A1 | 3/2005 | Falahee |
| 2006/0247673 A1 | 11/2006 | Voegele et al. |
| 2012/0089093 A1 | 4/2012 | Trusty |
| 2013/0184536 A1 | 7/2013 | Shibley et al. |
| 2014/0330285 A1 | 11/2014 | Rosenblatt et al. |
| 2016/0158468 A1 | 6/2016 | Tang et al. |
| 2017/0049427 A1 | 2/2017 | Do et al. |
| 2017/0325657 A1 | 11/2017 | Prior |
| 2018/0008250 A1 | 1/2018 | Joseph |
| 2018/0049771 A1 | 2/2018 | Rhemrev-Pieters |

\* cited by examiner

*Primary Examiner* — Sameh R Boles
(74) *Attorney, Agent, or Firm* — Carter, DeLuca & Farrell LLP

(57) ABSTRACT

A tissue guard includes a body having a proximal end portion and a distal end portion. The body includes an inner body defining a passageway therethrough and an outer body disposed about the inner body such that an annular flow channel is defined therebetween. A proximal lip extends radially outwardly from the proximal end portion of the body. A plurality of ribs is disposed within the annular flow channel and arranged to define a helical configuration to establish a helical fluid flow path through the annular flow channel upon application of suction therethrough.

10 Claims, 4 Drawing Sheets

TISSUE GUARD FOR TISSUE REMOVAL AND OTHER SURGICAL PROCEDURES

FIELD

The present disclosure relates to tissue removal and, more particularly, to tissue guards and systems incorporating the same for use in tissue removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard including a body having a proximal end portion and a distal end portion. The body includes an inner body defining a passageway therethrough and an outer body disposed about the inner body such that an annular flow channel is defined therebetween. A proximal lip extending radially outwardly from the proximal end portion of the body. A plurality of ribs is disposed within the annular flow channel and arranged to define a helical configuration to establish a helical fluid flow path through the annular flow channel upon application of suction therethrough.

In an aspect of the present disclosure, the annular channel defines an open distal end and a closed proximal end.

In another aspect of the present disclosure, the proximal lip extends from the inner body. In such aspects, the outer body may be joined with the proximal lip at the proximal end portion of the body to close a proximal end of the annular flow channel.

In yet another aspect of the present disclosure, the plurality of ribs is disposed on an inwardly-facing surface of the outer body.

In still another aspect of the present disclosure, the tissue guard further includes a connector disposed in fluid communication with the annular flow channel and extending proximally from the body.

In still yet another aspect of the present disclosure, the connector extends at least partially about a circumference of the body in a similar direction as the helical fluid flow path.

In another aspect of the present disclosure, wherein the proximal lip includes a plurality of spaced-apart cut-outs defined about the outer circumference of the lip to define a plurality of tabs of the lip, each tab including an outer edge segment.

In yet another aspect of the present disclosure, the proximal lip and the inner body are monolithically formed with one another as a single component. In such aspects, the outer body may be attached to the single component.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
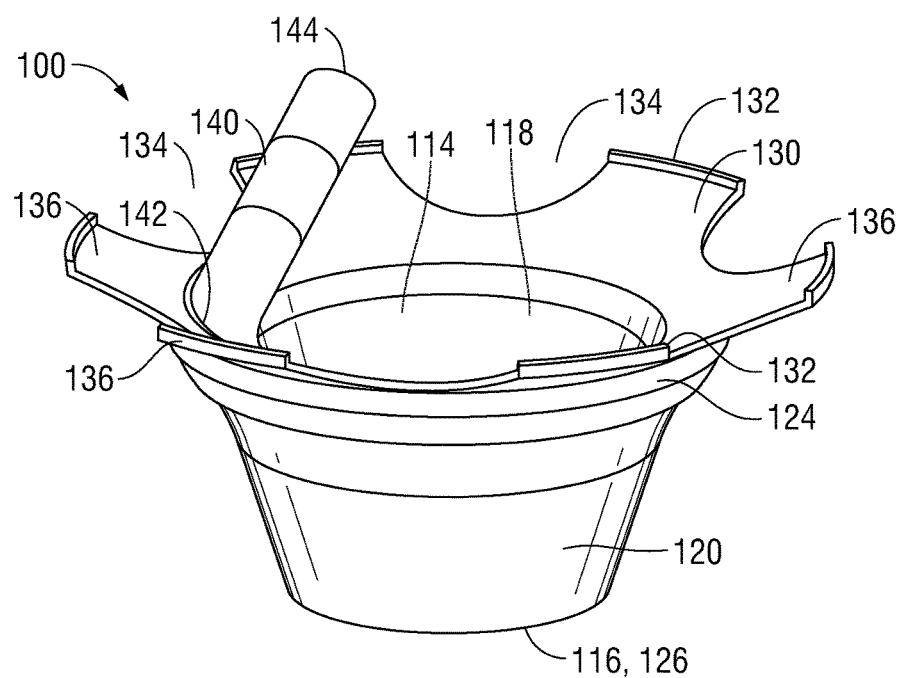
FIG. 1 is a side, perspective view of a tissue guard provided in accordance with aspects of the present disclosure.
Figure 2:
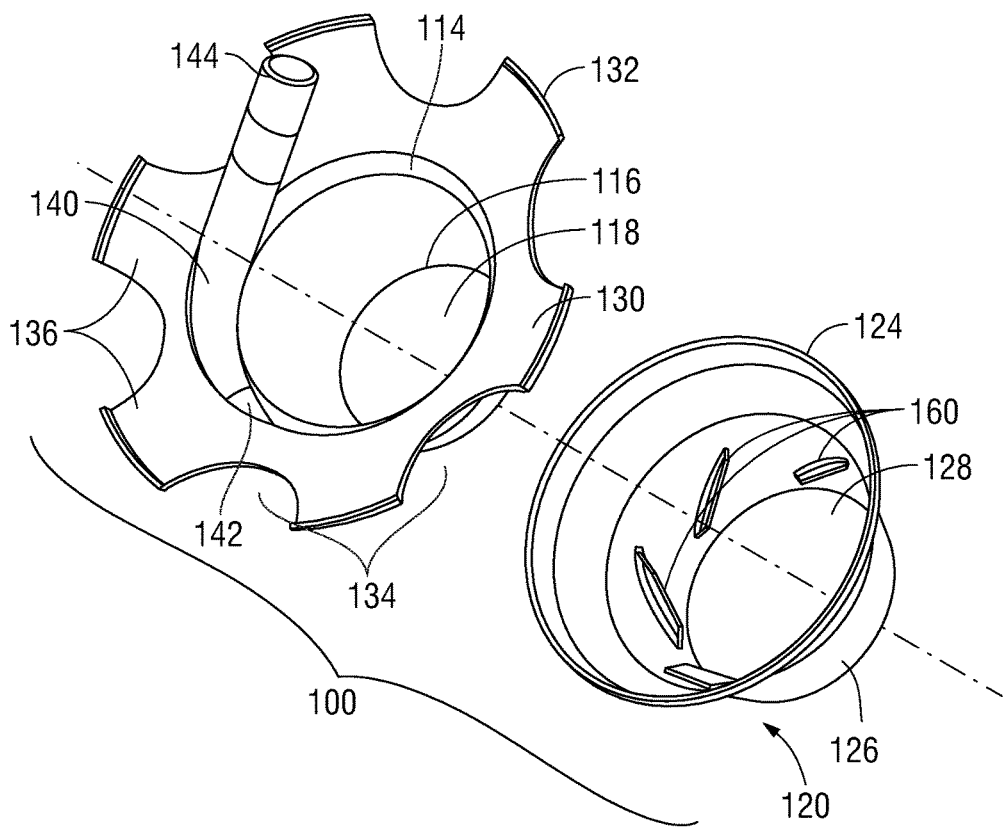
FIG. 2 is a top, perspective, exploded view of the tissue guard of FIG. 1.

Referring to FIGS. 1 and 2, a tissue guard provided in accordance with the present disclosure is shown generally identified by reference numeral 100. Tissue guard 100 is formed from a suitable material, e.g., a biocompatible plastic such as, for example, polyethylene, polycarbonate, etc., from any suitable method, e.g., injection molding a single component or multiple components permanently secured or releasably engagable with one another. The material, thickness, and configuration of tissue guard 100 are selected such that tissue guard 100 defines sufficient stiffness to maintain its shape when positioned within an opening in tissue "T" (FIG. 5) and/or when engaged within an access device 250 (FIG. 3B). However, the material, thickness, and configuration of tissue guard 100 also provide sufficient resilient flexibility to permit manipulation of tissue guard 100 from an at-rest position for insertion into an opening in tissue "T" (FIG. 5) and/or for engagement within access device 250 (FIG. 3B), with tissue guard 100 returning to or towards the at-rest position after insertion and/or engagement. Further, the material, thickness, and configuration of tissue guard 100 is selected such that tissue guard 100 is configured to withstand cutting and puncturing by surgical knives, scalpels, pencils, and the like, thereby protecting surrounding tissue "T" (FIG. 5) and/or access device 250 (FIG. 3B) from being cut or punctured. Tissue guard 100 may additionally or alternatively be configured to inhibit transfer of thermal and/or electrical energy therethrough to protect surrounding tissue "T" (FIG. 5) and/or access device 250 (FIG. 3B) from thermal and/or electrical energy.

Continuing with reference to FIGS. 1 and 2, tissue guard 100 includes an inner body 110, an outer body 120, a proximal lip 130, and a connector 140. Inner body 110 and proximal lip 130 may be monolithically formed as a single component, e.g., via injection molding, while outer body 120 is formed as a separate component, e.g., via injection molding, that is permanently secured, e.g., welded, to proximal lip 130 or that is releasably engagable therewith, e.g., via snap-fitting, threaded engagement, etc.

Inner body 110 defines an open proximal end portion 114, an open distal end portion 116, and a lumen 118 extending therethrough between open proximal and distal end portions 114, 116, respectively. Lumen 118 is configured to receive one or more surgical instruments (not shown) therethrough. In embodiments, inner body 110 defines a funnel-shaped configuration wherein a diameter of inner body 110 at open proximal end portion 114 thereof is greater than a diameter of inner body 110 at open distal end portion 116 thereof.

Proximal lip 130 of tissue guard 100 extends radially outwardly from open proximal end portion 114 of inner body 110 about the annular perimeter thereof. In this manner, proximal lip 130 extends radially outwardly from lumen 118. Proximal lip 130 may extend radially outwardly from inner body 110 at an oblique angle relative thereto, e.g., from about 90 degrees to about 135 degrees. Proximal lip 130 defines a circumferential outer edge 132. A plurality of spaced-apart cut-outs 134 are defined about the outer circumference of proximal lip 130, thereby interrupting outer edge 132 such that proximal lip 130 defines a plurality of spaced-apart tabs 136. Cut-outs 134 facilitate flexion of proximal lip 130, e.g., to facilitate insertion into an opening in tissue "T" (FIG. 5) and/or engagement within access device 250 (FIG. 3B).

Referring still to FIGS. 1 and 2, connector 140 defines a tubular configuration, is disposed at least partially within lumen 118, and extends proximally from lumen 118. Connector 140, more specifically, includes a first end portion 142 that is disposed in fluid communication, e.g., via an aperture (not shown) defined through inner body 110, with a flow channel 150 (FIGS. 3B and 5) defined between an exterior of inner body 110 and an interior of outer body 120. A second end portion 144 of connector 140 is proximally-spaced from inner body 110 and is configured to connect to tubing, e.g., tubing 610 (FIG. 6), to enable smoke to be evacuated from an internal surgical site through flow channel 150 (FIGS. 3B and 5), to connector 140, to the tubing 610 (FIG. 6), as detailed below. First end portion 142 of connector 140 may extend annularly along a portion of the inner circumference of lumen 118 to maintain the direction of flow of evacuated smoke. That is, as detailed below, tissue guard 100 is configured to establish a helical vortex flow of smoke to be evacuated from the internal surgical site via flow channel 150. By arranging first end portion 142 of connector 140 to extend in an annular manner, a smoother transition from flow channel 150 to connector 140 is achieved with minimal disruption of the flow of evacuated smoke.

Outer body 120 of tissue guard 100 defines an open proximal end portion 124, an open distal end portion 126, and a lumen 128 extending therethrough between open proximal and distal end portions 124, 126, respectively. Outer body 120 is disposed about (permanently or releasably) inner body 110 with inner body 110 received within lumen 128. Outer body 120 defines a diameter less than inner body 110 such that an annular flow channel 150 is defined therebetween. In embodiments, outer body 120 defines a funnel-shaped configuration complementary to that of inner body 110, e.g., wherein a diameter of outer body 120 at open proximal end portion 124 thereof is greater than a diameter of outer body 120 at open distal end portion 126 thereof. Proximal end portion 124 of outer body 120 is engaged (permanently or releasably) with a distally-facing surface of proximal lip 130 to close off flow channel 150 at the proximal end. Instead, smoke evaluated through flow channel 150 is directed into connector 140. Distal end portion 126 of outer body 120 remains open and radially-spaced from distal end portion 116 of inner body 110 to enable smoke to be drawn proximally into flow channel 150 from any position annularly about the circumference of the distal end of tissue guard 100.

Figure 5:
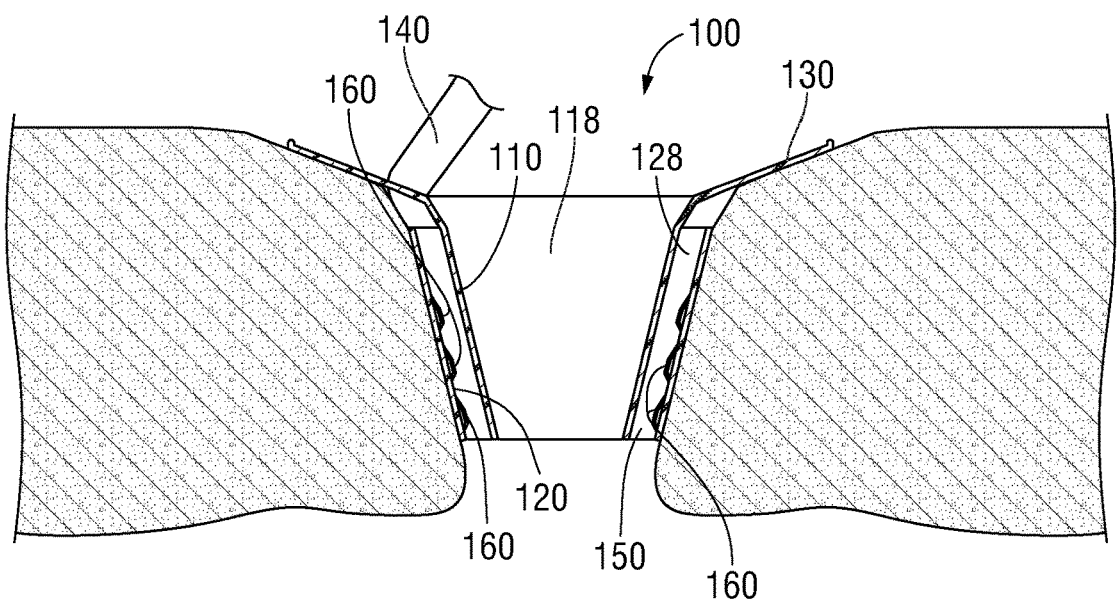
FIG. 5 is a cross-sectional view of the tissue guard of FIG. 1 disposed within an opening in tissue.

Referring also to FIGS. 3B and 5, outer body 120 further includes a plurality of ribs 160 disposed on an inwardly-facing surface thereof such that ribs 160 are disposed within flow channel 150. Alternatively or additionally, ribs 160 may be disposed on an outwardly-facing surface of inner body 120 to likewise be disposed within flow channel 150. Ribs 160 may be formed as protrusions formed with and extending from outer body 120, may be attached to outer body 120, or may be disposed within flow channel 150 in any other suitable manner. Ribs 160 are arranged relative to one another and outer body 120 to define a helical configuration to direct smoke in a helical vortex flow pattern as the smoke is evacuated from the internal surgical site via flow channel 150.

Figure 3A:
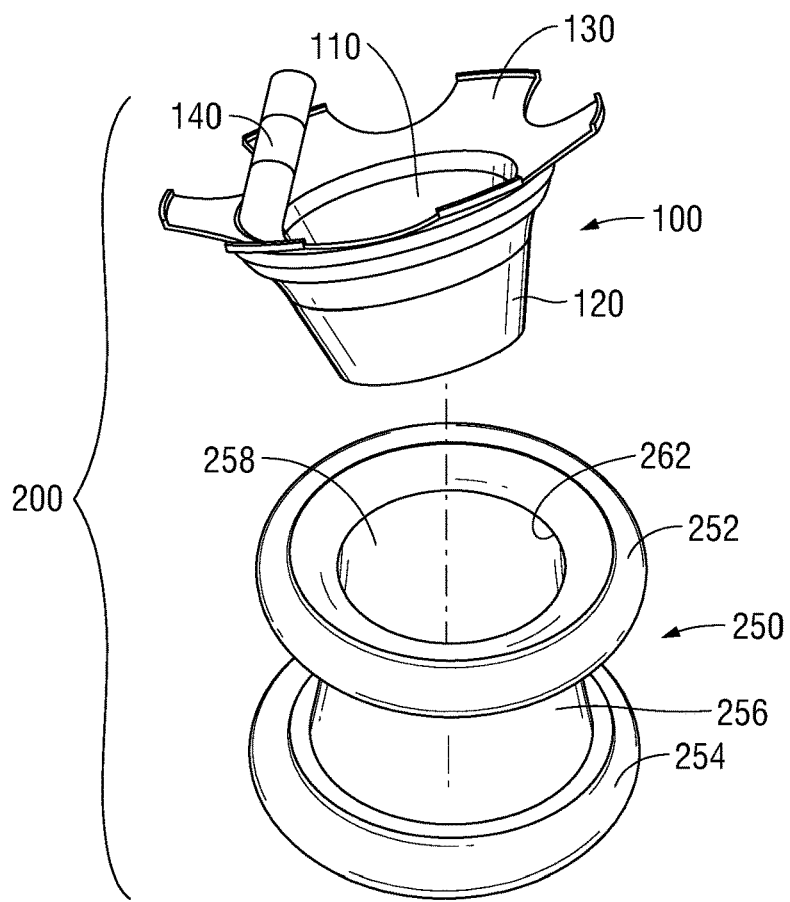
FIG. 3A is an exploded, top, perspective view of a system provided in accordance with the present disclosure including an access device and the tissue guard of FIG. 1.
Figure 3B:
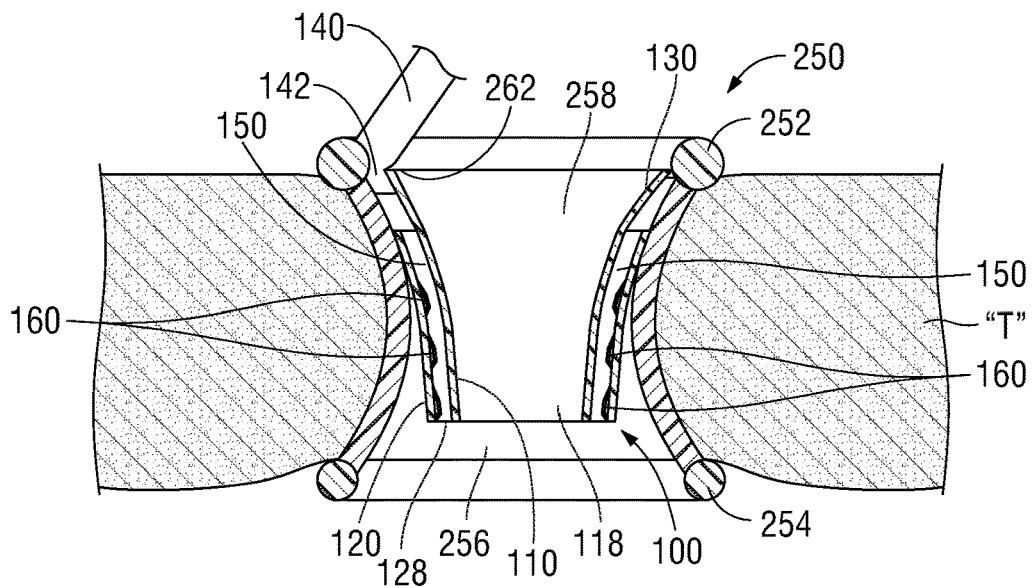
FIG. 3B is a cross-sectional view of the system of FIG. 3A disposed within an opening in tissue.

With reference to FIGS. 3A and 3B, a system 200 provided in accordance with the present disclosure includes tissue guard 100 and an access device 250. Access device 250 may be configured as a tissue retractor, an access port, or other suitable access device configured for positioning within an opening in tissue "T," e.g., a surgical incision or a naturally-occurring orifice, to provide access therethrough into an internal surgical site. Access device 250 includes a proximal rim 252 configured for positioning on an external side of the opening in tissue "T," a distal rim 254 configured for positioning on an internal side of the opening in tissue "T," and a body 256 extending between proximal and distal rims 252, 254, respectively. Body 256 is configured to extend through the opening in tissue "T" and defines a passageway 258 extending longitudinally therethrough to permit access to an internal surgical site through the opening in tissue "T." At least a portion of body 256 of access device 250 may be flexible to facilitate insertion and positioning of access device 250 within the opening in tissue "T." In embodiments, body 256 is formed from a flexible sleeve of material including one or more layers of material. Further, access device 250 may be selectively adjustable, e.g., by rolling proximal rim 254 distally about body 256, to retract tissue "T" and/or secure access device 250 within the opening in tissue "T." Access device 250 further defines an inwardly-extending overhang 262 between proximal rim 254 and body 256 and extending annularly about passageway 258.

As shown in FIG. 3B, in use, access device 250 is positioned within an opening in tissue "T" such that, as noted above, distal rim 254 is disposed on an internal surface of tissue "T" on the internal side of the opening in tissue "T," body 256 extends through the opening in tissue "T," and proximal rim 252 is disposed on an exterior surface of tissue "T" on the external side of the opening in tissue "T." As also noted above, access device 250 may be adjusted to conform access device 250 to a patient's anatomy, retracting tissue "T" and/or securing access device 250 within the opening in tissue "T."

With access device 250 disposed within the opening in tissue "T," tissue guard 100 is inserted into passageway 258 and is flexed or otherwise manipulated to permit proximal lip 130 to pass distally through proximal rim 252 and into passageway 258. Once tissue guard 100 is inserted sufficiently into passageway 258 of access device 250 such that proximal lip 130 is disposed distally of proximal rim 252, tissue guard 100 may be released, allowing tabs 136 of proximal lip 130 to engage overhang 262, thereby locking tissue guard 100 in engagement within access device 250.

With tissue guard 100 engaged within access device 250 as detailed above, surgical instrumentation may be inserted through lumen 118 of inner body 110 of tissue guard 100 into the internal surgical site to, for example, extract a tissue specimen therefrom. Tissue guard 100, as noted above, protects tissue "T" as well as access device 250 during the insertion, manipulation, use and withdrawal of any such surgical instrumentation.

In embodiments, it may be desirable to withdraw smoke or other fluid from the internal surgical site. For example, electrosurgical instrumentation may be utilized to electrically or electromechanically cut tissue to facilitate withdrawal of a tissue specimen, thereby generating smoke within the internal surgical site. In such instances, a source of suction may be attached to connector 140 to establish suction through connector 140 and flow channel 150. Due to the helical configuration of ribs 160, suction is established and smoke is evacuated in a helical vortex flow pattern from the internal surgical site, through flow channel 150, to connector 140.

Figure 4:
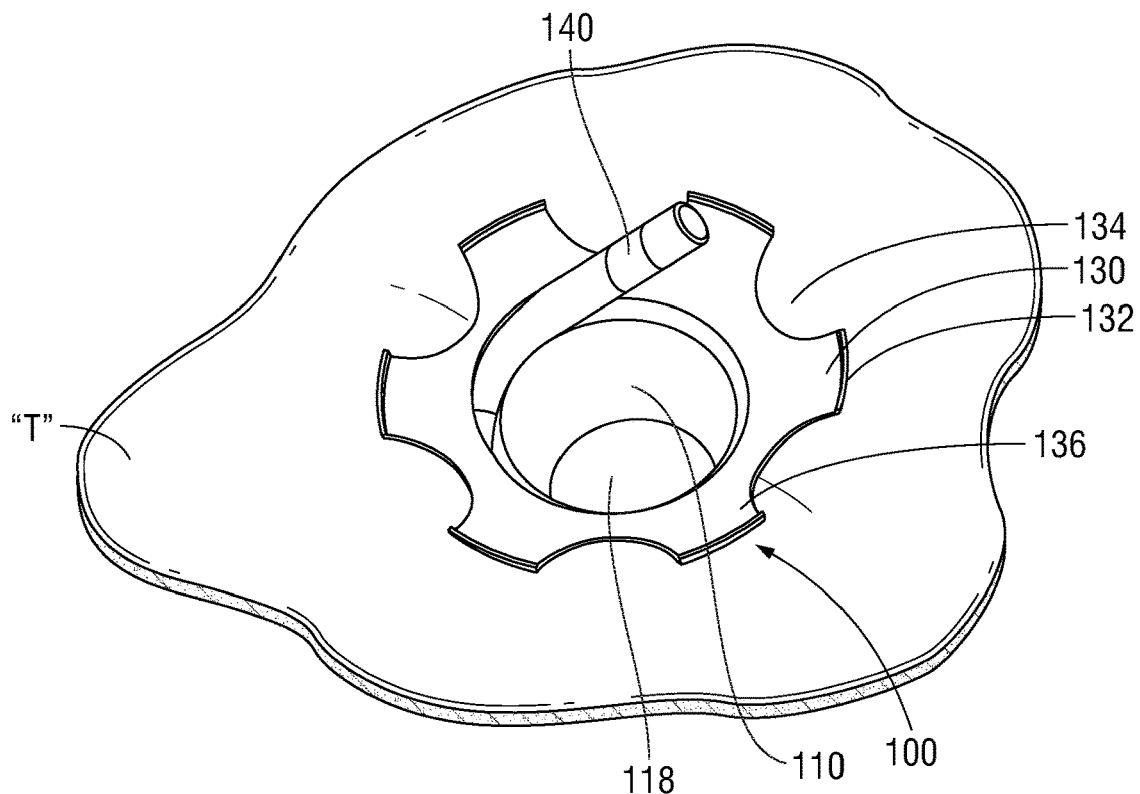
FIG. 4 is a top, perspective view of the tissue guard of FIG. 1 disposed within an opening in tissue.

Referring to FIGS. 4 and 5, tissue guard 100 is shown in use engaged within an opening in tissue "T." More specifically, tissue guard 100 is positioned with inner and outer bodies 110, 120, respectively, extending at least partially through the opening in tissue "T," while proximal lip 130 extends radially outwardly from the opening in tissue "T" about the external surface of tissue "T." Depending upon the size of the opening in tissue "T," outer body 120 may press against and/or retract tissue "T" surrounding the opening in tissue "T" to maintain and/or enlarge the opening in tissue "T." The use of tissue guard 100 may otherwise be similar as detailed above.

Figure 6:
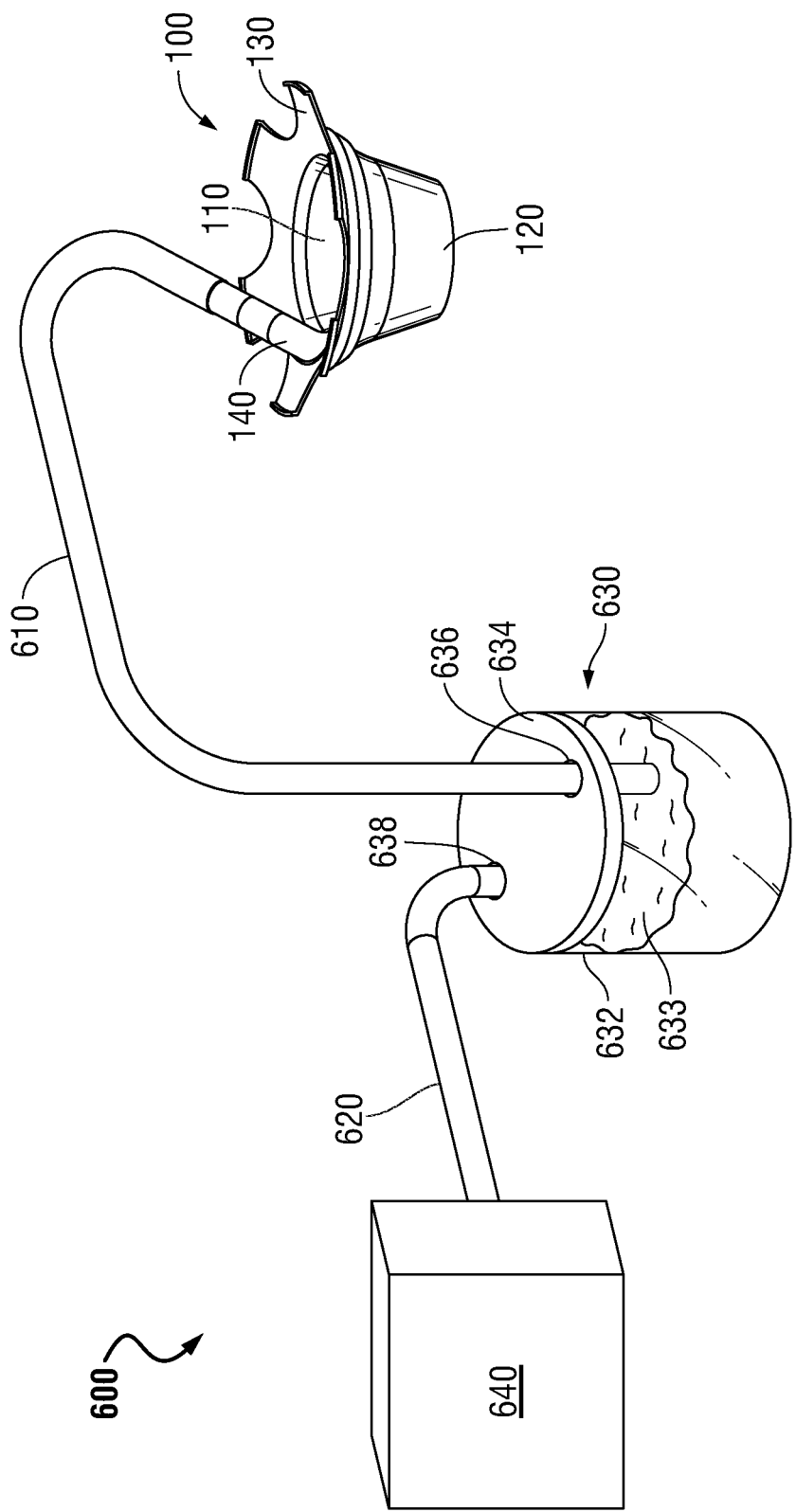
FIG. 6 is another system provided in accordance with the present disclosure including the tissue guard of FIG. 1, tubing, a collection reservoir, and a smoke evacuation source.

Turning to FIG. 6, a smoke evacuation system 600 provided in accordance with the present disclosure is shown generally including tissue guard 100, tubing 610, 620, a collection reservoir 630, and a smoke evacuation (or vacuum) source 640. Tissue guard 100 is detailed above; tubing 610 is attached at one end to connector 140 of tissue guard 100, as also detailed above. The other end of tubing 610 extends into collection reservoir 630 in sealing relation therewith.

Collection reservoir 630 includes a base 632 and a lid 634 sealed about base 632. Lid 634 defines first and second ports 636, 638 configured to receive ends of tubing 610, 620, respectively, in sealing relation therewith. These ends of tubing 610, 620 extend into the interior volume 633 of base 632 and are spaced-apart from one another as well as the bottom of base 632. Tubing 620 extends from collection reservoir 630 to smoke evacuation source 640 wherein the other end of tubing 620 is coupled to smoke evacuation source 640. In this manner, upon activation of smoke evacuation source 640, suction is established and smoke is evacuated in a helical vortex flow pattern from the internal surgical site through flow channel 150 (see FIGS. 3B and 5), then through connector 140, tubing 610, collection reservoir 630, tubing 620, to smoke evacuation source 640. During use, this suction, in addition to evacuating smoke, liquids, tissue, and/or debris may also be suctioned through tubing 610. However, as a result of the ends of tubing 610, 620 being spaced-apart from one another within collection reservoir 630 and spaced-apart from the bottom of base 632 of collection reservoir 630, the liquids, tissue, and/or debris are suctioned into collection reservoir 630 and deposited therein, while only the smoke and other gaseous fluids are further suctioned from collection reservoir 630 through tubing 620 to smoke evacuation source 640. Alternatively, tubing 610 may directly connect smoke evacuation source 640 with tissue guard 100 without the use of collection reservoir 630.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
    a body having a proximal end portion and a distal end portion and including:
        an inner body defining a passageway therethrough; and
        an outer body disposed about the inner body such that an annular flow channel is defined therebetween;
    a proximal lip extending radially outwardly from the proximal end portion of the body; and
    a plurality of ribs disposed within the annular flow channel and arranged to define a helical configuration to establish a helical fluid flow path through the annular flow channel upon application of suction therethrough.

2. The tissue guard according to claim 1, wherein the annular channel defines an open distal end and a closed proximal end.

3. The tissue guard according to claim 1, wherein the proximal lip extends from the inner body.

4. The tissue guard according to claim 3, wherein the outer body is joined with the proximal lip at the proximal end portion of the body to close a proximal end of the annular flow channel.

5. The tissue guard according to claim 1, wherein the plurality of ribs is disposed on an inwardly-facing surface of the outer body.

6. The tissue guard according to claim 1, further comprising a connector disposed in fluid communication with the annular flow channel and extending proximally from the body.

7. The tissue guard according to claim 6, wherein the connector extends at least partially about a circumference of the body in a similar direction as the helical fluid flow path.

8. The tissue guard according to claim 1, wherein the proximal lip includes a plurality of spaced-apart cut-outs defined about the outer circumference of the lip to define a plurality of tabs of the lip, each tab including an outer edge segment.

9. The tissue guard according to claim 1, wherein the proximal lip and the inner body are monolithically formed with one another as a single component.

10. The tissue guard according to claim 9, wherein the outer body is attached to the single component.

\* \* \* \* \*